(12) United States Patent
Remmereit

(10) Patent No.: US 8,697,670 B2
(45) Date of Patent: Apr. 15, 2014

(54) COMPOSITIONS AND METHODS OF TREATING VIRAL INFECTIONS

(75) Inventor: Jan Remmereit, Volda (NO)

(73) Assignee: Life Science Nutrition AS, Hovdebygda (NO)

( * ) Notice: Subject to any disclaimer, the term of this patent is extended or adjusted under 35 U.S.C. 154(b) by 93 days.

(21) Appl. No.: 12/695,417

(22) Filed: Jan. 28, 2010

(65) Prior Publication Data
US 2010/0190744 A1    Jul. 29, 2010

Related U.S. Application Data

(60) Provisional application No. 61/147,889, filed on Jan. 28, 2009.

(51) Int. Cl.
*A61K 31/70* (2006.01)

(52) U.S. Cl.
USPC .......................................................... 514/54

(58) Field of Classification Search
USPC .......................................................... 514/54
See application file for complete search history.

(56) References Cited

U.S. PATENT DOCUMENTS

| | | | |
|---|---|---|---|
| 6,127,113 A | 10/2000 | Atkinson | |
| 6,541,046 B2 * | 4/2003 | Wei et al. ...................... | 424/756 |
| 6,664,050 B1 | 12/2003 | Atkinson | |
| 7,422,750 B2 | 9/2008 | Umeda | |
| 7,901,715 B2 | 3/2011 | Remmereit | |
| 2003/0181416 A1 | 9/2003 | Comper | |
| 2006/0193907 A1 | 8/2006 | Remmereit | |
| 2009/0221526 A1 | 9/2009 | Remmereit | |
| 2010/0119558 A1 | 5/2010 | Remmereit | |
| 2010/0190744 A1 | 7/2010 | Remmereit | |

FOREIGN PATENT DOCUMENTS

| | | |
|---|---|---|
| CA | 2520757 | 3/2007 |
| EP | 00293826 | 5/1989 |
| EP | 1773363 | 4/2007 |
| JP | 01031707 | 2/1989 |
| JP | 01085905 | 3/1989 |
| JP | 01313433 | 12/1989 |
| WO | 2006017943 | 2/2006 |
| WO | 2006020210 | 2/2006 |
| WO | 2007086658 | 8/2007 |
| WO | 2008122098 | 10/2008 |
| WO | 2010052575 | 5/2010 |
| WO | 2010086746 | 8/2010 |

OTHER PUBLICATIONS

Atkinson et al., 1997, "Production of obesity in mice with a human virus." Int. J. of Obesity 21: S36.
Atkinson et al., 1998, "Evidence for an association of an obesity virus with human obesity at three sites in the United States." Int. J. Obesity 22: S57.
Brandley et al., 1987, "Multiple carbohydrate receptors on lymphocytes revealed by adhesion to immobilized polysaccharides." J. Cell Biol. 105: 991-997.
Carter et al., 1983, "Influence of diet on a retrovirus-induced obesity and stunting syndrome.", Avian Dis. 27: 317-322.
Carter et al., 1983, "Rous-associated virus type 7 induces a syndrome in chickens characterized by stunting and obesity.", Infect. Immun. 39: 410-422.
Dhurandhar et al., 1992, "Effect of adenovirus infection on adiposity in chicken." Vet. Microbiol. 31: 101-107.
Dhurandhar et al., 1996, "Development of obesity in chickens after infection with a human adenovirus." Obesity Res 4:24S.
Dhurandhar et al., 1997, "Evidence for an association of a virus with obesity in humans." FASEB J 3: A230.
Dhurandhar et al., 2000, "Increased adiposity in animals due to a human virus." Int. J. Obesity 24: 989-996.
Frankel et al., 1993, "Inhibition of human LDL oxidation by resveratrol." Lancet 341: 1104.
Goldberg et al., 1995, "A Global Survey of Trans-Resveratrol Concentrations in Commercial Wines." Am. J. Enol. Vitic. 46(2): 159-165.
Gosztonyi et al., 1995, "Borna disease—neuropathology and pathogenesis." Current Topics in Microbiol. Immunol. 190: 39-73.
Itoh et al., 1995, "Immunological analysis of inhibition of lung metastases by fucoidan (GIV-A) prepared from brown seaweed *Sargassum thunbergii*." Anticancer Res. 15: 5b 1937-1947.
Lee et al., 1994, "Protection of cell injury against oxidative stress by reserveratrol." Society for Neuroscience Abstracts 20(1-2): 1648.
Lyons et al., 1982, "A virally induced obesity syndrome in mice." Science 216: 82-85.
Pace-Asciak et al., 1995, "The red wine phenolics trans-resveratrol and quercetin block human platelet aggregation and eicosanoid synthesis: implications for protection against coronary heart disease." Clinica Chimica Acta 235:207-219.
Patankar et al., 1993, "A revised structure for fucoidan may explain some of its biological activities." J. Biol. Chem. 268: 21770-21776.
Riou, 1996,"Antitumor and antiproliferative effects of a fucan extracted from *Ascophyllum nodosum* against a non-small-cell bronchopulmonary carcinoma line." Anticancer Res. 16: 3a 1213-1218.
Soeda et al, 2000, "Oversulfated fucoidan inhibits the basic fibroblast growth factor-induced tube formation by human umbilical vein endothelial cells: its possible mechanism of action." Biochim. Biophysica Acta (1): 127-134.
Soleas et al., 1995, "A Derivatized Gas Chromatographic-Mass Spectrometric Method for the Analysis of Both Isomers of Resveratrol in Juice and Wine." Am. J. Enol. Vitic. 46(3): 346-352.
Yang et al., 2008, "Enhanced inhibition of adipogenesis and induction of apoptosis in 3T3-L1 adipocytes with combinations of resveratrol and quercetin", Life Sciences, 82: 1032-9.

* cited by examiner

*Primary Examiner* — Elli Peselev
(74) *Attorney, Agent, or Firm* — Casimir Jones SC

(57) ABSTRACT

The present invention relates to the field of nutraceuticals, and in particular to nutraceuticals comprising sulfated polysaccharides, *Astragalus* polysaccharides, resveratrol, and combinations thereof. These compositions find use in inducing physiological responses such, decreasing body fat, increasing lean body mass, alleviating the symptoms of colds, preventing the onset of colds, increasing energy, increasing the feeling of well-being in subjects, and improving skin tone and appearance.

14 Claims, 11 Drawing Sheets

Figure 5. Initial screening of APS (1 mg/ml) for weaker antiviral activity

| APS titer ($\log_{10}$ TCID$_{50}$/ml) | Control virus titer ($\log_{10}$ TCID$_{50}$/ml) | Virus reduction (%) |
|---|---|---|
| 8.5 | 10 | 96.84 |

Figure 7. Antiviral activity of APS (1 mg/ml) by TCID method

| | Conditions | Sample titer ($\log_{10}$ TCID$_{50}$/ml) | Control virus titer ($\log_{10}$ TCID$_{50}$/ml) | Virus reduction (%) |
|---|---|---|---|---|
| A | Cells and virus pretreat APS+incubate in APS | 7.4 | 7.6 | 36.90 |
| B | Cells pretreat APS | 6.6 | 7.6 | 81.52 |
| C | Incubate in APS | 7.8 | 7.6 | 0 |
| D | Cells pretreat APS+incubate in APS | 8 | 7.6 | 0 |

COMPOSITIONS AND METHODS OF TREATING VIRAL INFECTIONS

CROSS REFERENCE TO RELATED APPLICATIONS

This application claims the benefit of U.S. Provisional Patent Application Ser. No. 61/147,889, filed: Jan. 28, 2009, the entire contents of which are incorporated herein by reference.

FIELD OF THE INVENTION

The present invention relates to the field of nutraceuticals, and in particular to nutraceuticals comprising sulfated polysaccharides, *Astragalus* polysaccharides, resveratrol, and combinations thereof. These compositions find use in inducing physiological responses such, decreasing body fat, increasing lean body mass, alleviating the symptoms of colds, preventing the onset of colds, increasing energy, increasing the feeling of well-being in subjects, and improving skin tone and appearance.

BACKGROUND OF THE INVENTION

Obesity is a prevalent nutritional disorder in the United States. Obesity in childhood, adolescence, and adulthood represents a serious concern and a challenge to the medical and lay communities. Major impacts include effects on blood pressure, intermediary metabolism, respiratory function, psychological well-being, social adaptation, and educational performance. Obesity is associated with significant adult morbidity, including long-term effects on cardiovascular health and premature mortality.

Accumulation of excess fat mass occurs when total energy intake exceeds total energy expenditure, including the energy allowance for normal growth. This energy imbalance can result from excessive energy intake and/or reduced energy expenditure for body metabolism, thermoregulation, and physical activity. Increases in energy intake are observed in genetic syndromes, such as Prader-Willi syndrome, Cushing syndrome, and drug-induced obesity. Reductions in energy expenditure characterize hormonal deficiency states, including hypothyroidism and growth hormone deficiency.

The etiology of obesity is considered to be multifactorial. Animal obesity has been classified into nine different groups, including obesity of neural, endocrine, pharmacological, nutritional, environmental, seasonal, genetic, idiopathic or of viral origin (see, e.g., Sclaffini, A. (1984) Int. J. Obesity 8: 491-508; herein incorporated by reference in its entirety). While genetic and behavioral components of obesity have been the focus of intense study, six pathogens have been reported to cause obesity in animal models (see, e.g., Atkinson R. L., et al., (1997) Int. J. of Obesity 21:S36; Carter J. K., et al., (1983) Infect. Immun. 39:410-422; Carter J. K., et al., (1983) Avian Dis 27:317-322; Dhurandhar N. V., et al., (1990) J. Bombay Vet. College 2:131-132; Dhurandhar N. V., et al., (1992) Vet. Microbiol. 31:101-107; Dhurandhar N. V., et al., (1996) Obesity Res 4:24S; Dhurandhar N. V., et al., (2000) Int. J. Obesity 24:989-996; Gosztonyi G., et al., (1995) Current Topics in Microbiol. Immunol. 190:39-73; Lyons M. J., et al., (1982) Science 216:82-85; each herein incorporated by reference in their entireties). Indeed, the human adenovirus Ad-36 is implicated in causing obesity in humans (see, e.g., Atkinson R. L., et al., (1998) Int. J. Obesity 22:S57; Dhurandhar N. V., et al., (1997) FASEB J 3:A230; each herein incorporated by reference in their entireties).

Treatment options for virally induced obesity is limited to traditional approaches (e.g., diet management, exercise management, lifestyle management, surgery, and anorectic agents (e.g., phentermine, phenylpropanolamine, mazindol, ephedra, and sibutramine)). What is needed are improved methods of treating obesity.

SUMMARY OF THE INVENTION

The present invention relates to the field of nutraceuticals, and in particular to nutraceuticals comprising sulfated polysaccharides, *Astragalus* polysaccharides, resveratrol, and combinations thereof. These compositions find use in inducing physiological responses such, decreasing body fat, increasing lean body mass, alleviating the symptoms of colds, preventing the onset of colds, increasing energy, increasing the feeling of well-being in subjects, and improving skin tone and appearance.

In some embodiments, the present invention provides methods of inducing a physiological effect selected from the group consisting increasing lean body mass, decreasing body fat, increasing energy, increasing the feeling of well-being, alleviation of cold symptoms, and improving the skin tone, roughness and appearance in a subject comprising: providing a composition comprising a sulfated polysaccharide, and administering said composition to said patient under conditions such that said physiological effect is induced. The present invention is not limited to any particular delivery method. In some embodiments, the composition is delivered orally. In some embodiments, the composition is administered topically. In some embodiments, the composition is delivered as a cosmetic composition. In some embodiments, the composition is administered in a daily dosage of from 3 to 5 grams.

In some embodiments, the symptom is obesity. In some embodiments, the methods further comprise administering an antibiotic. In some embodiments, the methods further comprise administering an antiviral pharmaceutical agent. In some embodiments, the methods further comprise administering an anorectic agent.

In some embodiments, the administration of said composition induces weight reduction in a subject. In some embodiments, the administration of said composition increases the lean body mass of said subject. In some embodiments, the administration of said composition reduces cellulite in said subject. In some embodiments, the administration of said composition improves skin tone in said subject. In some embodiments, the administration of said composition improves skin tightness in said subject. In some embodiments, the administration of said composition improves skin roughness in said subject. In some embodiments, the administration of said composition reduces body fat in said subject.

In some embodiments, the composition is a dietary supplement. In some embodiments, the composition is a nutritional supplement. In some embodiments, the composition is provided in a food or a drink.

The present invention is not limited to the use of any particular sulfated polysaccharide. In some embodiments, the sulfated polysaccharide is selected from the group consisting of fucan, chondroitin sulfate, heparin sulfate, dermatan sulfate, dextran sulfate, and keratin sulfate. The present invention is not limited to the use of any particular fucan. In some embodiments, the fucan is a fucoidan. The present invention is not limited to any particular fucoidan composition. In some embodiments, the fucoidan is from a natural source. In some embodiments, the said natural source is selected from the group consisting of marine brown algae and sea cucumbers.

In some embodiments, the present invention provides methods of inducing a physiological effect selected from the group consisting of alleviation of the symptoms of viral induced obesity, preventing viral induced obesity increasing lean body mass, decreasing body fat, increasing energy, increasing the feeling of well-being, alleviation of cold symptoms, and improving the skin tone, roughness and appearance in a subject comprising: providing a composition comprising at least one of a sulfated polysaccharide, *Astragulus* polysaccharide and resveratrol, and orally administering said composition to said patient under conditions such that said physiological effect is induced. In some embodiments, the symptom is obesity. In some embodiments, the methods comprise administering an agent selected from the group consisting of a flavonoid and a sialic acid. In some embodiments, the composition comprises effective amounts of said sulfated polysaccharide, said *Astragulus* polysaccharide and said resveratrol. In some embodiments, the administration of said composition induces weight reduction in a subject. In some embodiments, the administration of said composition increases the lean body mass of said subject. In some embodiments, the administration of said composition reduces cellulite in said subject. In some embodiments, the administration of said composition improves a skin parameter selected from the group consisting of improved skin tone, improved skin tightness in said subject and improved skin roughness. In some embodiments, the administration of said composition reduces body fat in said subject. In some embodiments, the composition is a dietary supplement. In some embodiments, the composition is a nutritional supplement. In some embodiments, the composition is provided in a food or a drink. In some embodiments, the sulfated polysaccharide is selected from the group consisting of fucan, chondroitin sulfate, heparin sulfate, dermatan sulfate, dextran sulfate, and keratin sulfate. In some embodiments, the fucan is a fucoidan. In some embodiments, the fucoidan is from a natural source selected from the group consisting of marine brown algae and sea cucumbers. In some embodiments, the fucoidan is administered in a daily dosage of from 3 to 5 grams. In some embodiments, the resveratrol is administered in a daily dosage of from about 1 mg to 50 mg. In some embodiments, the *Astragalus* polysaccharide is administered in a daily dosage of from 0.5 to 5 grams.

In some embodiments, the present invention provides compositions comprising an effective amount of at least two of a sulfated polysaccharide, *Astragalus* polysaccharide and resveratrol. In some embodiments, the composition is formulated for oral delivery. In some embodiments, the composition is formulated for topical delivery.

DESCRIPTION OF THE FIGURES

FIG. 5. Initial screening of APS (1 mg/ml) for weaker antiviral activity.

DEFINITIONS

Figure 1:
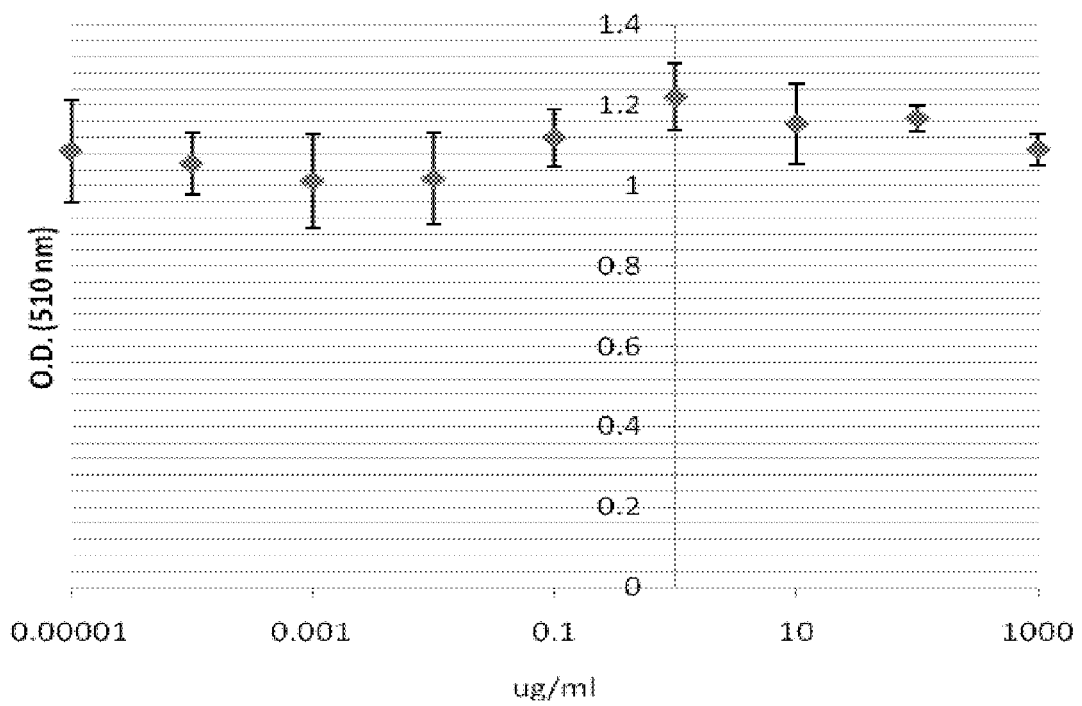
FIG. 1. APS cytotoxicity in A549 cells.

As used herein, the term "sulfated polysaccharide" refers to a polysaccharide that comprises sulfate groups.

As used herein, the term "*astragalus* polysaccharide" refers to polysaccharides obtained from the root of the *astragalus* plant.

As used herein, the term "resveratrol" refers to a phytoalexin produced naturally by several plants that is also known as trans-3,5,4'-Trihydroxystilbene, trans-Resveratrol and (E)-5-(p-Hydroxystyryl) resorcinol (E)-5-(4-hydroxystyryl)benzene-1,3-diol.

As used herein, the term "sialic acid" refers to N- or O-substituted derivatives of neuraminic acid, including, but not limited to, N-acetylneuraminic acid (NANA), n-glycolylneraminic acid (NGNA), and 2-keto-3-deoxynonic acid (KDN).

As used herein, the term "obesity" and related terms refers to an increase in body weight beyond the limitation of skeletal and physical requirement, as the result of an excessive accumulation of fat in the body.

As used herein, the term "body fat" refers to the total amount of fat in a subject's body, and is often expressed as a percentage of the total mass of the subject.

As used herein, the term "lean body mass" refers to the mass of a subject minus mass associated with fat content, and is often expressed as a percentage of total mass of a subject. "Lean body mass" is generally the mass of the bone, organs, muscle and proteins of the body such as collagen.

As used herein, the term "anorectic agent" and related terms refer to pharmaceutical agents used to induce weight loss in a subject. Examples of anorectic agents include, but are not limited to, phentermine, phenylpropanolaminea, mazindol, ephedra, and sibutramine.

As used herein, the term "phytonutrient" refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

As used herein, the term "functional foods" refers to food products that include biologically active nutraceutical agents.

As used herein, the terms "nutraceutical agent," and related terms, refer to natural, bioactive chemical compounds that have health promoting, disease preventing or medicinal properties. Examples of nutraceutical agents include, but are not limited to, *Allium Cepa, Allium Sativum, Aloe Vera, Angelica* Species, Naturally Occurring Antioxidants, *Aspergillus Oryzae* Enzyme Therapy, barley grass, Bromelain, Carnitine, Carotenoids and Flavonoids, Catechin, *Centella Asiatica* (*Gotu kola*), Coenzyme Q10, Chinese Prepared Medicines, *Coleus Forskohlii, Commiphora Mukul, Crataegus Oxyacantha* (Hawthorne), *Curcuma Longa* (Turmeric), *Echinacea* Species (Purple Coneflower), *Eleutherococcus Senticosus* (Siberian Ginseng), *Ephedra* Species, Dietary Fish Oil Consumption and Fish Oil Supplementation, Genistein, *Ginkgo Biloba, Glycyrrhiza* (Licorice), *Hypericum Perforatum* (St. John's Wort), *Hydrastis* (Goldenseal) and Other Berberine-Containing Plants, *Lactobacillus, Lobelia* (Indian Tobacco),

*Melaleuca Alternifolia, Mentha Piperita*, NGNA, *Panax* Ginseng, Pancreatic Enzymes, *Piper Mythisticum*, Procyanidolic Oligomers, *Pygeum Africanum, Quercetin, Sarsaparilla* Species, *Serenoa Repens* (Saw palmetto, *Sabal serrulata*), *Silybum Marianum* (Milk Thistle), Rosemary/Lemon balm, Selenite, Tabebuia Avellanedae (LaPacho), *Taraxacum Officinale, Tanacetum Parthenium* (Feverfew), Taxol, *Uva Ursi* (Bearberry), *Vaccinium Myrtillus* (Blueberry), *Valerian Officinalis, Viscum Album* (Mistletoe), Vitamin A, Beta-Carotene and Other Carotenoids, and *Zingiber Officinale* (Ginger).

As used herein, the term "weight loss diet regimen" or related terms, is used broadly to include any type of weight loss plan used by a subject. Examples of weight loss diet regimens include, but are not limited to, Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, Zone diet, running, swimming, meditation, yoga, hypnosis, clinical therapy, bicycling, walking, hypnosis, rehabilitory training, a dietary plan provided through a dietician, and surgical procedures.

As used herein, the terms "subject" and "patient" refer to any animal, such as a mammal like a dog, cat, bird, livestock, and preferably a human. Specific examples of "subjects" and "patients" include, but are not limited to, individuals suffering from viral obesity.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "dietary supplement" refers to a small amount of a compound for supplementation of a human or animal diet packaged in single or multiple does units. Dietary supplements do not generally provide significant amounts of calories but may contain other micronutrients (e.g., vitamins or minerals).

As used herein, the term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

DETAILED DESCRIPTION OF THE INVENTION

The present invention relates to the field of nutraceuticals, and in particular to nutraceuticals comprising sulfated polysaccharides. Compositions comprising sulfated polysaccharides find use in inducing physiological responses such as, such as alleviating the symptoms of viral-induced obesity, preventing viral-induced obesity, decreasing body fat, increasing lean body mass, alleviating the symptoms of colds, preventing the onset of colds, increasing energy, increasing the feeling of well-being in subjects, and improving skin tone and appearance.

In the U.S., the prevalence of obesity increased by 30% from 1980 to 1990, and this increase appears to be continuing. One etiology of human obesity is of infectious origin (see, e.g., Dhurandhar, N. (2001) J. Nutr. 131: 2794S-2797S; herein incorporated by reference in its entirety). Six pathogens are reported to cause obesity in animals. Canine distemper virus was the first virus reported to cause obesity in mice (see e.g., Lyons M., et al., (1982) Science 216:82-85; Bernard A., et al., (1988) Comp. Biochem. Physiol. 91B:691-696; Bernard A., et al., (1991) Virology 313:545-551; Bernard A., et al., (1993) J. Neuropath. Exp. Neuro. 52:471-480; McFerran J., et al., (1975) Am. J. Vet. Res. 36:527-534; Bernard A., et al., (1999) J. Virology 73(9):7317-7327; each herein incorporated by reference in their entireties), followed by the avian retrovirus Rous-associated virus-7 shown to cause stunting, obesity and hyperlipidemia in chickens (see e.g., Carter J. K., et al., (1983) Infect. Immun. 39:410-422; Carter J. K., et al., (1983) Avian Dis 27:317-322; each herein incorporated by reference in their entireties). The obesity-promoting effect of Borna disease virus has been demonstrated in rats (see e.g., Gosztonyi G. & Ludwig H. (1995) Current Topics in Microbiol. Immunol. 190:39-73; Fabricant C. G., et al., (1983) Federation Proc 42:2476-2479; each herein incorporated by reference in their entireties). Scrapie agents were reported to induce obesity in mice and hamsters (see e.g., Kim Y. S., et al., (1987) J. Infect. Dis. August; 156(2):402-405; Carp R. L., et al., (1990) J. Infect. Dis. 161(3):462-466; Carp R. L., et al., (1998) J. Gen. Virol. 79(Pt 11):2863-2869; Kim Y. S., et al., Proc. Soc. Exp. Biol. Med. 189(1):21-27; each herein incorporated by reference in their entireties). The final two reports were of SMAM-1, an avian adenovirus (see e.g., Dhurandhar N. V., et al., (1990) J. Bombay Vet. College 2:131-132; Dhurandhar N. V., et al., (1992) Vet. Microbiol. 31:101-107; Ajinkya S. M. (1985) Final Technical Report, ICAR 1985: 13-43 Red and Blue Cross Publishing Bombay, India; each herein incorporated by reference in their entireties), and Ad-36 (see e.g., Dhurandhar N. V., et al., (2000) Int. J. Obesity 24:989-996; Dhurandhar N. V., et al., (2001) Int. J. Obesity 25:990-996; Kolesar J. M., et al., (2000) J. Chromatog. B. 744:1-8; herein incorporated by reference in its entirety), a human adenovirus that caused obesity in animals. Additionally, an association with human obesity is the unique feature of SMAM-1 (see, e.g., Dhurandhar N. V., et al., (1997) Obesity Res 5:464-469; herein incorporated by reference in its entirety) and Ad-36 (see, e.g., Vangipuram, S. D., et al., (2004) Obesity Research 12:770-777; Dhurandhar, N. V., et al., (2002) J. Nutr. 132:3155-3160; Atkinson R. L., et al., (1998) Int. J. Obesity 22:S57; Dhurandhar N. V., et al. (1997) FASEB J 3:A230; Atkinson R. L., et al., (2000) Int. J. Obesity suppl 1:S39; Dhurandhar N. V., et al.; (1999) FASEB J 13(4): A369; each herein incorporated by reference in their entireties).

U.S. Pat. Nos. 6,127,113 and 6,664,050, each herein incorporated by reference in their entireties, characterize Ad-36 induced viral obesity. In particular, humans who suffer from viral obesity (i.e., obesity caused by a virus) have, on the average, significantly lower triglycerides (TG), cholesterol (CHOL) and low-density-lipoprotein-associated cholesterol (LDL-CHOL) levels than persons who suffer from obesity that is not viral. In fact, the average TG, CHOL and LDL-CHOL levels of persons with viral obesity are within the normal ranges for persons who are not obese. Diagnostic and screening approaches for Ad-36 and Ad-36p are provided. Anti-obesity vaccines, wherein inactivated viral nucleic acid (e.g., Ad-36 nucleic acid) is administered to a subject, are also described.

A. *Astragalus* Polysaccharides

*Astragalus membranaceus* (Latin): membranous milk-vetch root (English), huang qi (Chinese), ogi (Japanese), and hwanggi (Korean) is one of the important "Qi tonifying" adaptogenic herbs from the Chinese materia medica. The Chinese species *A. membranaceus* and the related *A. membranaceus* var *mongholicus* (synonym: *A. mongholicus*) are defined in the Pharmacopoeia of the People's Republic of China as Radix Astragali. It has been prescribed for centuries for general weakness, chronic illnesses, and to increase overall vitality. The genus *Astragalus* is a very large group of more than 2,000 species distributed worldwide, and is commonly known as milk-vetch root. Currently, much of the pharmacological research on *Astragalus* is focused on its immune-stimulating polysaccharides and other active ingredients useful in treating immune deficiency conditions. *Astragalus* has demonstrated a wide range of potential therapeutic applications in immunodeficiency syndromes, as an adjunct cancer therapy, and for its adaptogenic effect on the heart and kidneys. *Astragalus* root has been used to promote immune function and as a tonic to build stamina. Ancient Chinese texts record the use of *Astragalus* for tonifying the spleen, blood, and qi.

The polysaccharides found in *Astragalus* have received a great deal of attention, especially the polysaccharide fraction F3. They have been shown to play a role in immunomodulatory actions. Polysaccharides A, B, and C have been identified as glucans, and polysaccharide D as a heteropolysaccharide. *Astragalus* polysaccharides (APS) are preferably extracted from the root of the *Astragalus* plant. APS useful in the present inventions are generally at least of 50%, 60%, 65%, 70%, 80% or 90% purity. APS may be obtained, for example, from Hongsheng Bioprosucts Co., Xi'an, China, Shaanxi Scidoor Hi-Tech Biology Co., Ltd., (China) and Huzhou Linyin Biological Co., Ltd. (China), among others.

In preferred embodiments, an effective amount of the sulfated polysaccharide to cause the desired physiological response is provided to the subject, preferably in a once a day or twice a day dosage. In preferred embodiments, an effective amount of the APS is from 0.1-10 grams of the APS, and most preferably from 0.5-5 grams of the APS or 0.5 to 3 grams of the APS daily. In some embodiments, the effective amount is the amount necessary to prevent viral-induced obesity, treat viral-induced obesity, reduce the symptoms of viral induced obesity, decrease body fat as a percentage of total body mass, increase lean body mass as a percentage of total body mass, reduce or alleviate cold symptoms, prevent the onset of colds, increase the energy of subjects, increase the feeling of well-being of subjects, and improve skin tone, roughness, and appearance. In some preferred embodiments, the APS is provided in conjunction with a sulfated polysaccharide and/or resveratrol as described in detail below.

B. Sulfated Polysaccharides

The present invention contemplates the use of nutraceutical and cosmeceutical compositions comprising sulfated polysaccharides to treat viral-induced obesity, decrease body fat, increase lean body mass, alleviate the symptoms of colds, prevent the onset of colds, increasing energy, increase the feeling of well-being in subjects, and improve skin tone, roughness and appearance.

Sulfated polysaccharides useful in the present invention include, but are not limited to, fucan, chondroitin sulfate, heparin sulfate, dermatan sulfate, dextran sulphate, carrageenan (e.g., kappa or iota), cellulose sulfate, keratin sulfate, galactan sulfates, rhamnan sulfates, spirulans, ulvans, and xylomannan sulfates. In preferred embodiments, the fucan is fucoidan or a derivative of fucoidan. In some embodiments, the fucoidan is F-fucoidan, which is >95% composed of sulfated esters of fucose, U-fucoidan, which is approximately 20% glucuronic acid, or mixtures thereof. Fucans (including fucoidan) are high molecular weight sulfated polysaccharides extracted from brown seaweeds. These compounds reportedly have multiple inhibitory actions in vivo and in vitro including anti-thrombin, anti-proliferative, anti-complement, anti-cancer and anti-neutrophil migration effects. Fucans may block various binding events at cell surfaces including cell-cell binding through integrin-selectin molecules, or by binding thrombin or complement in the blood or fucose receptors on cell surfaces. In some preferred embodiments, the sulfated polysacchariade employed is greater than about 70%, 80%, 90%, 95% or 99% pure.

Such activity is thought to be responsible for anti-inflammatory properties via (for example) inhibition of lymphocyte or neutrophil binding to vascular endothelial cells that might prevent the invasion of these cells into a tissue compartment with subsequent inflammation. Patankar, M. S., et al., J. Biol. Chem. 268: 21770 21776 (1993); Brandley, B. K., et al., J. Cell Biol. 105: 991 997 (1987). Recent studies have also shown that Fucans inhibit vascular smooth muscle cell proliferation, Logeart, D., et al., Eur. J. Cell Biol. 74: 376 384 & 385 390 (1997), indicating (but not demonstrating) a possible anti-restenosis potential of these compounds. Fucans have been shown to be slowly internalized in cells following surface binding to both endothelial and smooth muscle cells. Glabe, C. G., et al., J. Cell Science 61: 475 490 (1983); Logeart, D., et al., Eur. J. Cell Biol. 74: 376 384 (1997). Riou, D., et al., Anticancer Res., 16 (3A): 1213 1218 (1996); Itoh, H., Anticancer Res., 13 (6A): 2045 2052 (1993); Nishiro, T., et al., Thromb. Res., 62: 765 773 (1991); Blondin, C., et al., Mol. Immunol., 31: 247 253 (1994); Patankar, M. S., et al., J. Biol. Chem., 268: 21770 21776 (1993). In Japan, fucoidan extracted from various seaweeds is marketed as a health food. Fucoidan has been proposed as a cosmetic or dermal agent. JP 01031707 and JP 01085905. Fucoidan has been reported to be a potential anticancer agent. Riou. D., Anticancer Res. 16: 3a 1213 18 (1996); Itoh, H., et al., Anticancer Res., 15: 5b 1937 47 (1995). Fucoidan was reported to not inhibit angiogenesis in vitro. Soeda, S., et al., Biochim. Biophysica Acta (1): 127 134 (2000).

Similarly, fucoidan was found to stimulate HUVEcell proliferation (in vitro) induced by serum, indicating a possible proangiogenic effect (although inhibition was possible when fibroblast growth factor was present). Giraux, J., et al., Eur. J. Cell Biol. 77 4: 352 9 (1998). Studies have also shown that Fucans inhibit endothelial cell monolayer binding. Glabe, C. G., J. Cell Science, 61: 475 490 (1983). Since the cells that make up capillaries are endothelial cells, this report indicates that in vitro, some aspects of cell adhesion may be inhibited but these data do not demonstrate any in vivo antiangiogenic effect of fucoidan. Fucoidan has been reported to inhibit the binding of *helicobacter* to gastric cells hinting at an antigastric ulcer effect. Shibat, H. J., Nutr. Sci. Vitaminol. 45: 325 336 (1999).

Other sulfated polysaccharides including branched and linear types are reported to have differential anticoagulant activity. Pereira, M. S., J. Biol. Chem. 12: 7656 67 (1999). Dextran sulphate and derivatives have been reported to inhibit cancer cell growth, Bittoun, P., Carbohydrate Res. (3 4): 247 255 (1999) and to have anticoagulant effects, Mauray, S., J.

Biomat. Sci. Poly ed. 9: 373 87 (1998). Sulphated polysaccharides have been proposed as anti-viral agents for use against e.g., AIDS. EP 00293826; JP 01313433.

The present inventors have shown that polysaccharides can be used to prevent viral-induced obesity, treat viral-induced obesity, reduce the symptoms of viral induced obesity, decrease body fat as a percentage of total body mass, increase lean body mass as a percentage of total body mass, reduce or alleviate cold symptoms, prevent the onset of colds, increase the energy of subjects, increase the feeling of well-being of subjects, and improve skin tone, roughness, and appearance. In preferred embodiments, an effective amount of the sulfated polysaccharide to cause the desired physiological response is provided to the subject, preferably in a once a day or twice a day dosage. In preferred embodiments, an effective amount of the sulfated polysaccharide, and in particularly preferred embodiments, fucoidan, is from 2-20 grams, 10-20 grams, and most preferably from 3-5 grams of the sulfated polysaccharide, daily. In some embodiments, the effective amount is the amount necessary to prevent viral-induced obesity, treat viral-induced obesity, reduce the symptoms of viral induced obesity, decrease body fat as a percentage of total body mass, increase lean body mass as a percentage of total body mass, reduce or alleviate cold symptoms, prevent the onset of colds, increase the energy of subjects, increase the feeling of well-being of subjects, and improve skin tone, roughness, and appearance.

Fucan sulfates from marine brown algae usually have complex and heterogeneous structures. Recent studies have also shown that these polysaccharides consistently contain a backbone of either -(13)-linked or alternating -(13)- and -(14)-linked L-fucopyranosyl residues with sulfate groups at position 4 (Daniel R, Berteau O, Jozefonvicz J, Goasdoue N. Degradation of algal (*Ascophyllum nodosum*) fucoidan by an enzyme activity contained in digestive glands of the marine mollusk *Pecten maxims*. Carbohydr Res (1999) 322(3-4): 291-297; Chevelot L, Foucault A, Chaubet F, Kervarec N, Sinquin C, Fisher A M, Boisson-Vidal C. Further data on the structure of brown seaweed fucans: Relationships with anticoagulant activity. Carbohydr Res (1999) 319:154-165; Patankar M S, Oehninger S, Barnett T, Williams R L, Clark G F. A revised structure for fucoidan may explain some of its biological activities. J Biol Chem (1993) 268:21770-21776; Cumashi A, Ushakova N A, Preobrazhenskaya M E, D'Incecco A, Piccoli A, Totani L, Tinari N, Morozevich G E, Berman A E, Bilan M I, et al. A comparative study of the anti-inflammatory, anti-coagulant, anti-angiogenic and anti-adhesive activities of nine different fucoidans from brown seaweeds. Glycobiology (2007) 17(5):541-552). This regular backbone is frequently masked by different substituents, such as monosaccharides (galactose, glucose, mannose, xylose, or glucuronic acid), acetyl groups, and/or sulfate esters. The matrix-phase polysaccharides of red seaweeds are linear sulfated galactans, which contain alternating β-(13)-D- and -(14)-galactopyranosyl residues (Percival E, McDowell R H. Chemistry and Enzymology of Marine Algal Polysaccharides (1967) London: Academic.; Rees D A. Structure, conformation and mechanism in the formation of polysaccharide gels and networks. Adv Carbohydr Chem Biochem (1969) 24:267-332; Painter T J. Algal polysaccharides. In: The Polysaccharides—Aspinall G O, ed. (1983) 2, 1st ed. New York: Academic. 195-285). These galactans differ in the configuration of the -linked units. If the configuration is L-type, the polymer is agaran; in the case of D-type, it is carrageenan. Different O-linked groups, such as sulfate esters, methyl ethers, pyruvate acetal, or monosaccharides, usually mask this regular backbone. Some of the -galactopyranosyl units may also occur in the 3,6-anhydro form. The third member of this class is DL-hybrid galactan sulfate, a polymer in which -linked units can have D- and L-configuration in the same molecule (Stortz Calif., Cerezo A S. Novel findings in carrageenans, agaroids and "hybrid" red seaweed galactans. Curr Top Phytochem (2000) 4:121-133). Other polysaccharides having potent in vitro antiviral activities include rhamnan sulfates, spirulans, ulvans, and xylomannan sulfates.

Fucoidan of the present invention is preferably extracted from natural sources such as brown seaweed. Useful sources of fucoidan include, but are not limited to, the following marine algaes: Laminariales, Chordariales, Fucales, and the like, such as *Kjellmaniella crassifolia, Laminaria japonica, Kjellmaniella, Fucus, Nemacystus, Cladosiphon okamuranus, Undaria, Undaria pinnatifida, Ecklonia kurome, Eisenia, Ecklonia*, Giant kelp, *Lessonia nigrescence, Cystoseira canariensis, Adenocystis utricularis*, and *Ascophyllum nodosum*. Sulfated polysaccharides derived from Rhodophyceae, for instance, sulfated polysaccharides derived from *Gelidiun amansii, Gracilaria*, and *Pteroclavia capillacae* have the same effects as those of the fucoidan used in the present invention, and can be also used in the present invention. In other preferred embodiments, the fucoidan is extracted from sea cucumbers.

In general, fucoidan extracts are prepared from the sources described above using three solvents, alone or in parallel; distilled water, 2% calcium chloride solution and diluted hydrochloric acid (pH 2.0) solution. Extraction is preferably at room temperature and then at 70 degrees C. The extraction yields and characteristics of the extracts are similar for the three processes, with only minor differences. In general, two different types of fucoidans are present in seaweed. One of them, mostly extracted at room temperature, is composed mainly of L-fucose, D-galactose and ester sulfate (the 'galactofucan'). The other product (the 'uronofucoidan') is the major component of the extracts obtained at 70 degrees C. It is composed mainly of fucose, accompanied by other monosaccharides (mostly Man, but also Glc, Xyl, Rha and Gal), significant amounts of uronic acids and low proportions of sulfate ester. Fractionation with the cationic detergent cetrimide allows achieving a better separation of the galactofucan and uronofucoidan components. See Ponce et al., Carbohydr. Res. 338(2):153-65 (2003). In some embodiments, the fucoidan is processed and/or incorporated into food products as described in U.S. Pat. No. 7,422,750, incorporated by reference herein in its entirety. In some embodiments, APS and resveratrol are incorporated into the products in effective amounts.

C. Resveratrol

Resveratrol (3,5,4'-trihydroxystilbene) has been identified as a constituent not only of grape skins (Soleas et al. (1995) Am. J. Enol. Vitic. 46(3):346-352) but has also been found to be present in ground nuts, eucalyptus, and other plant species. Goldberg et al. (1995), Am. J. Enol. Vitic. 46(2):159-165. A great deal of interest has been focused on the compound's antifungal activity and its correlation with resistance to fungal infection. Id. at 159. Resveratrol may be obtained commercially (typically as the trans isomer, e.g. from the Sigma Chemical Company, St. Louis, Mo.), or it may be isolated from wine or grape skins, or it may be chemically synthesized. Synthesis is typically carried out by a Wittig reaction linking two substituted phenols through a styrene double bond, as described by Moreno-Manas et al. (1985) Anal. Quim 81:157-61 and subsequently modified by others (Jeandet et al. (1991) Am. J. Enol. Vitic. 42:41-46; Goldberg et al. (1994) Anal. Chem. 66:3959-63).

There are more studies concerning trans-resveratrol than the cis isomer; however, the cis isomer also appears to be equally important from a biological standpoint. Numerous uses have been proposed and evaluated for the resveratrol isomers. Jang et al. (1997) Science 275:218-220, show that resveratrol has cancer chemopreventive activity in assays representing three major stages of carcinogenesis. That is, the authors found that the compound: (1) acted as an antioxidant and antimutagen and induced phase II drug-metabolizing enzymes ("anti-initiation" activity); (2) mediated anti-inflammatory effects and inhibited cyclooxygenase and hydroperoxidase ("antipromotion" activity); and (3) induced human promyelocytic leukemia cell differentiation ("antipromotion" activity). In addition, as noted above, resveratrol has been extensively studied for its correlation to the cardiovascular utility of red wine. See, e.g., Bertelli et al., supra; Pace-Asciak et al. (1995), Clinica Chimica Acta 235:207-2191; and Frankel et al. (Apr. 24, 1993), The Lancet 341:1104. Neurologic uses have also been proposed (Lee et al. (1994), Society for Neuroscience Abstracts 20(1-2): 1648).

Resveratrol may be administered in natural form, i.e., as isolated from grape skins, wine or other plant-derived compositions, or it may be administered as chemically synthesized in the laboratory (e.g., using the methods of Moreno-Manas et al., Jeandet et al., or Goldberg et al. Am. J Enol. Vitic. 46(2):159-165 (1994), or as obtained commercially, e.g., from the Sigma Chemical Company (St. Louis, Mo.).

The present inventors have found that resveratrol is especially effective in combination with the polysaccharides described above, and that dosages of resveratrol commonly included in many supplements are actually too high and can cause fatigue and depression. Accordingly, resveratrol is provided in a daily dosage of from 1 to 100 mg, from 1 to 50 mg, or from 1 to 20 mg daily. In some embodiments, the effective amount is the amount necessary to prevent viral-induced obesity, treat viral-induced obesity, reduce the symptoms of viral induced obesity, decrease body fat as a percentage of total body mass, increase lean body mass as a percentage of total body mass, reduce or alleviate cold symptoms, prevent the onset of colds, increase the energy of subjects, increase the feeling of well-being of subjects, and improve skin tone, roughness, and appearance, while not causing fatigue or depression.

D. Sialic Acids

In some embodiments, sialic acids are provided in combination with at least one of the sulfated polysaccharides, APS and resveratrol. Supplementation with NGNA is described in WO 06/020210, incorporated herein by reference in its entirety. Suitable sialic acids for use with the present invention include, but are not limited to, N-acetylneuraminic acid (NANA), n-glycolylneraminic acid (NGNA), and 2-keto-3-deoxynonic acid (KDN). In preferred embodiments, the present invention provides compositions comprising dietary supplements for inducing physiological responses such as alleviating the symptoms of viral-induced obesity, alleviating the symptoms of colds, preventing the onset of colds, increasing energy and increasing the feeling of well-being in subjects. Such compositions may contain, for example, between 0.1 g and 10.0 g of sialic acid, preferably between 0.5 g and 2.0 g of sialic acid, and even more preferably, approximately 1.0 g of sialic acid, in combination with one or more of sulfated polysaccharides, APS and resveratrol in amounts as described above.

E. Dietary Supplements

The present invention provides dietary supplements comprising at one of a sulfated polysaccharide, APS, and resveratrol. In some embodiments, the supplements comprise a combination of one or more of a sulfated polysaccharide, APS, and resveratrol, each provided in an effective amount. In some preferred embodiments, the sulfated polysaccharide is a fucoidan. In some embodiments, the supplements further comprise a sialic acid. Other nutraceuticals agents may also be included in the supplement. Nutraceutical agents are natural, bioactive chemical compounds that have health promoting, disease preventing or medicinal properties. Examples of nutraceuticals include, but are not limited to, *Allium cepa, Allium sativum, Aloe vera, Angelica* Species, Naturally Occurring Antioxidants, *Aspergillus oryzae*, barley grass, Bromelain, Carnitine, carotenoids and flavonoids, Catechin, *Centella asiatica (Gotu kola)*, Coenzyme Q10, Chinese Prepared Medicines, *Coleus forskohlii, Commiphora mukul*, Conjugated Linoleic Acids (CLAs), *Crataegus oxyacantha* (Hawthorne), *Curcuma longa* (Turmeric), *Echinacea* Species (Purple Coneflower), *Eleutherococcus senticosus* (Siberian Ginseng), *Ephedra* Species, Dietary Fish Oil, Genistein, *Ginkgo biloba, Glycyrrhiza* (Licorice), *Hypericum perforatum* (St. John's Wort), *Hydrastis* (Goldenseal) and other Berberine-containing plants, *Lactobacillus, Lobelia* (Indian Tobacco), *Melaleuca alternifolia, Menaquinone, Mentha piperita*, n-glycolylneuraminic acid (NGNA), *Panax Ginseng, Pancreatic Enzymes, Piper mythisticum, Procyanidolic Oligomers, Pygeum africanum, Quercetin, Sarsaparilla* species, *Serenoa repens* (Saw palmetto, *Sabal serrulata*), *Silybum marianum* (Milk Thistle), Rosemary/Lemon balm, Selenite, *Tabebuia avellanedae* (LaPacho), *Taraxacum officinale, Tanacetum parthenium* (Feverfew), *Taxol, Uva ursi* (Bearberry), *Vaccinium myrtillus* (Blueberry), *Valerian officinalis, Viscum album* (Mistletoe), Vitamin A, Beta-Carotene and other carotenoids, and *Zingiber officinale* (Ginger).

Several nutraceutical agents are used in treating viral disorders (e.g., Genistein (in soy/red clover), rosemary/lemon balm, selenite, barley grass, lauric acid, *Phyllanthus amarus/niruri* (see, e.g., Nicolson, G. (1998) J. Medicine 1:123-128; herein incorporated by reference in its entirety). Additional anti viral nutraceutical agents include, but are not limited to, catechins, flavonoids, especially luteolin, *Echinacea*, cascara, and NGNA. Preferably, NGNA is provided from sea cucumbers, e.g., an extract of sea cucumbers, or is prepared from chitin. In some embodiments, NGNA is prepared as described in WO 00/38967, incorporated by reference herein its entirety. For example, N-glycolylneuraminic acid can be purchased commercially from, for example, Sigma Chemical Company, St. Louis, Mo. N-glycolylneuraminic acid also can be synthesized. For example, CMP-N-acetylneuraminic acid hydroxylase can be used to synthesize N-glycolylneuraminic acid as its CMP-glycoside. See, Schlenzka et al., Glycobiolog, 1994, 4(5):675-683. Non-enzymatic methods of synthesis include, for example, synthesis from N-acetylneuraminic acid using methanol or hydrochloric acid and benzylalcohol. Other synthesis methods are described in Choi et al., J. Org. Chem., 1996, 61:8/39 (from mannosamine), Faillard et al., J. Physiol. Chem.' 1965, 344:167 (from glucosamine), U.S. Pat. No. 4,774,326 and U.S. Pat. No. 4,774,327, both of which are incorporated by reference herein in their entirety.

In preferred embodiments, the present invention provides compositions comprising at least one of a sulfated polysaccharide, APS and resveratrol and combinations thereof to prevent viral-induced obesity, treat viral-induced obesity, reduce the symptoms of viral induced obesity, decrease body fat as a percentage of total body mass, increase lean body mass as a percentage of total body mass, reduce or alleviate cold symptoms, prevent the onset of colds, increase the energy of subjects, increase the feeling of well-being of subjects, and improve skin tone, roughness, and appearance.

Such compositions may contain, for example, a daily dosage of between 2 g and 10.0 g of the sulfated polysaccharide (e.g., fucoidan) or between 10 and 20 g of the sulfated polysaccharide, preferably between 3.0 g and 5.0 g of the sulfated polysaccharide (e.g., fucoidan); a daily dosage of resveratrol of from 1 to 100 mg, from 1 to 50 mg, or from 1 to 20 mg daily; APS in a daily dosage of from 0.1-10 grams of the APS, and most preferably from 0.5-5 grams of the APS or 0.5 to 3 grams of the APS; and/or a daily dosage of a sialic acid of from between 0.1 g and 10.0 g of sialic acid, preferably between 0.5 g and 2.0 g of sialic acid, and even more preferably, approximately 1.0 g of sialic acid. Furthermore, the dietary supplement is preferably provided in an amount sufficient to induce the physiological response desired (e.g., to prevent viral-induced obesity, treat viral-induced obesity, reduce the symptoms of viral induced obesity, decrease body fat as a percentage of total body mass, increase lean body mass as a percentage of total body mass, reduce or alleviate cold symptoms, prevent the onset of colds, increase the energy of subjects, increase the feeling of well-being of subjects, and improve skin tone, roughness, and appearance). In some embodiments, the compositions are provided for use in inducing one of the foregoing responses, while in other embodiments, the compositions are provided for use in inducing two or more of the foregoing responses.

The present invention further provides methods for treating the physiological conditions discussed above (e.g., conditions such as obesity, periodic weight gain, lack of energy, mild depression, colds, etc.). In preferred embodiments, dietary supplements are used in treating viral induced obesity. In other preferred embodiments, dietary supplements are used in treating infection caused by a virus that causes viral obesity (e.g., Ad-36). In other preferred embodiments, dietary supplements are used in preventing viral related obesity through targeting of viruses that cause viral obesity (e.g., Ad-36, Ad-36p, SMAM-1). In some embodiments, the compositions are provided for use in treating one of the foregoing conditions, while in other embodiments, the compositions are provided for use in treating two or more of the foregoing conditions.

The dietary supplements of the present invention are further used in conjunction with a weight loss diet regimen. The present invention is not limited to a particular kind of weight loss diet regimen (e.g., exercise, reduced calorie intake, etc.). In preferred embodiments, the weight loss diet regimen is a dietary plan (e.g., Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, and Zone diet. In still other preferred embodiments, the weight loss diet regimen is an exercise plan (e.g., running, swimming, meditation, yoga, hypnosis, clinical therapy, bicycling, walking, etc.). In still other preferred embodiments, the weight loss diet regimen is a clinically assisted plan (e.g., hypnosis, rehabilitory training, a dietary plan provided through a dietician, surgical procedures, etc.).

The dietary supplements of the present invention may further be administered in any form (e.g., pill, food product, etc.). In preferred embodiments, the dietary supplements are provided as a beverage, bar, powder, pill, or shake (e.g., a nutritional supplement as described in more detail below).

The dietary supplements of the present invention may be taken one or more times daily. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day (e.g., approximately 3-5 g of a sulfated polysaccharide) in a reasonable number of units (e.g., two capsules or tablets taken twice a day). In preferred embodiments, the doses add up each day to the daily intake of each ingredient. In preferred embodiments, the dietary supplements are taken with meals or before meals. In other embodiments, the dietary supplements are not taken with meals. In preferred embodiments, a dietary supplement increases satiety and results in a decrease in caloric intake and subsequent weight loss. In particularly preferred embodiments, a dietary supplement regulates viruses (e.g., adenoviruses).

F. Delivery of Dietary Supplements

Dietary supplements of the present invention may be delivered in any suitable format, including, but not limited to, dermal delivery, oral delivery, or mucosal delivery. In preferred embodiments, dietary supplements are formulated for oral delivery. In preferred embodiments, the APS, sulfated polysaccharide, and/or resveratrol utilized for delivery is greater than about 60%, 70%, 80%, 90%, 95% or 99% pure.

The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Maack Publishing Co., Easton, Pa.).

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

G. Topical Delivery

In some embodiments, sulfated polysaccharides, APS and/or resveratrol are formulated for topical delivery and/or for use as cosmetic agents. The amount of the active ingredient(s) (i.e., sulfated polysaccharide, APS, and/or resveratrol) is preferably 0.001 to 50% by mass, more preferably 0.1 to 20% by mass, still more preferably 1 to 15% by mass and particularly preferably 3 to 10% by mass relative to each cosmetic.

The active ingredients may be combined in the cosmetic by dissolution in an oil-soluble base or an oil-soluble component. The method for producing the cosmetic of the present invention using the defined active ingredients is not particularly limited, and the active ingredients can be dissolved in a nonionic surfactant, lower alcohol, polyvalent alcohol, or natural fat or oil such as olive oil, squalane, a fatty acid or a higher alcohol.

Examples of nonionic surfactants include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate); glycerine/polyglycerine fatty acids (e.g., mono-cottonseed oil fatty acid glycerine, glycerine monoerucate, glycerine sesquioleate, glycerine monostearate, glycerine .alpha.,.alpha.'-oleate pyroglutamate, glycerine monostearate malic acid); propylene glycol fatty acid esters (e.g., monostearic acid propylene glycol); cured castor oil derivatives; and glycerine alkyl ether.

Examples of POE-based hydrophilic nonionic surfactants include POE-sorbitan fatty acid esters (e.g., POE-sorbitan monooleate, POE-sorbitan monostearate, POE-sorbitan monooleate, POE-sorbitan tetraoleate); POE-sorbit fatty acid esters (e.g., POE-sorbit monolaurate, POE-sorbit monooleate, POE-sorbit pentaoleate, POE-sorbit monostearate); POE-glycerine fatty acid esters (e.g., POE-glycerine monostearate, POE-glycerine monoisostearate, POE-glycerine triisostearate, POE-monooleate); POE-fatty acid esters (e.g., POE-distearate, POE-monodioleate, distearic acid ethylene glycol); POE-alkyl ethers (e.g., POE-lauryl ether, POE-oleyl ether, POE-stearyl ether, POE-behenyl ether, POE-2-octyldodecyl ether, POE-cholestanol ether); Pluronic types (e.g., Pluronic); POE/POP-alkyl ethers (e.g., POE/POP-cetyl ether, POE/POP-2-decyltetradecyl ether, POE/POP-monobutyl ether, POE/POP-hydrogenated lanoline, POE/POP-glycerine ether); tetra-POE/tetra-POP-ethylenediamine condensates (e.g., Tetronic); POE-castor oil cured castor oil derivatives (e.g., POE-castor oil, POE-cured castor oil, POE-cured castor oil monoisostearate, POE-cured castor oil triisostearate, POE-cured castor oil pyroglutamate monoisostearate diester, POE-cured castor oil maleate); POE-beeswax lanoline derivatives (e.g., POE-sorbit beeswax); alkanol amide (e.g., palm oil fatty acid diethanolamide, lauric acid monoethanolamide, fatty acid isopropanolamide); POE-propylene glycol fatty acid ester; POE-alkylamine; POE-fatty acid amide; sucrose fatty acid ester; alkylethoxydimethylamine oxide; and trioleyl phosphate.

Examples of lower alcohols include ethanol, propanol, isopropanol, isobutyl alcohol and t-butyl alcohol.

Examples of polyvalent alcohols include bivalent alcohols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol); trivalent alcohols (e.g., glycerine, trimethylolpropane); tetravalent alcohols (e.g., pentaerythritols such as 1,2,6-hexanetriol); pentavalent alcohols (e.g., xylitol); hexavalent alcohols (e.g., sorbitol, mannitol); polyvalent alcohol polymers (e.g., diethylene glycol, dipropylene glycol, triethylene glycol, polypropylene glycol, tetraethylene glycol, diglycerine, polyethylene glycol, triglycerine, tetraglycerine, polyglycerine); bivalent alcohol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether); bivalent alcohol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether); bivalent alcohol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate); glycerine monoalkyl ethers (e.g., chimyl alcohol, selachyl alcohol, bathyl alcohol); sugars and sugar alcohols (e.g., sorbitol, maltitol, maltotriose, mannitol, sucrose, erythritol, glucose, fructose, starch-degraded sugar, maltose, xylitose, starch-degraded sugar-reduced alcohol); glysolid; tetrahydrofurfuryl alcohol; POE-tetrahydrofurfuryl alcohol; POP-butyl ether; POP/POE-butyl ether; tripolyoxypropylene glycerine ether; POP-glycerine ether; POP-glycerine ether phosphate; POP/POE-pentaerythritol ether, and polyglycerine.

Examples of oils include animal and plant oils such as avocado oil, olive oil, sesame oil, camellia oil, evening primrose oil, turtle oil, macadamia nut oil, corn oil, mink oil, rapeseed oil, egg yolk oil, parsic oil, wheat germ oil, sasanqua oil, castor oil, flaxseed oil, safflower oil, cotton seed oil, perilla oil, soybean oil, peanut oil, tea oil, kaya seed oil, rice bran oil, China wood oil, jojoba oil, cacao butter, fractionated coconut oil, horse oil, palm oil, palm kernel oil, beef tallow, mutton tallow, lard, lanoline, whale wax, beeswax, carnauba wax, vegetable wax, candelilla wax and squalane, cured oils thereof, mineral oils such as liquid paraffin and petrolatum, and synthetic triglycerines such as tripalmitate glycerine.

Examples of the fatty acid include lauric acid, myristic acid, palmitic acid, oleic acid, linoleic acid, linolenic acid, stearic acid, behenic acid, 12-hydroxystearic acid, isostearic acid, undecynoic acid, tolic acid, eicosapentaenoic acid and docosahexaenoic acid. Examples of the higher alcohol include lauryl alcohol, cetyl alcohol, stearyl alcohol, behenyl alcohol, myristyl alcohol, oleyl alcohol, cetostearyl alcohol, jojoba alcohol, lanoline alcohol, batyl alcohol, 2-decyltetradecanol, cholesterol, phytosterol and isostearyl alcohol. Examples of the synthetic ester include cetyl octanoate, octyldodecyl myristate, isopropyl myristate, myristyl myristate, isopropyl palmitate, butyl stearate, hexyl laurate, decyl oleate, dimethyloctanoic acid, cetyl lactate and myristyl lactate. Examples of the silicone include chain-shaped polysiloxanes such as dimethyl polysiloxane and methylphenyl polysiloxane, cyclic polysiloxanes such as decamethyl cyclopolysiloxane, and three-dimensional mesh structures of silicone resins.

The skin care cosmetics of the present invention include milky lotions, beauty liquids, creams, lotions, skin care oils, cleansing oils, bath oils, or facial washes, makeup removers, shampoos and body soaps.

H. Nutritional Supplements

In other embodiments, the present invention provides nutritional supplements (e.g., energy bars or meal replacement bars or beverages) comprising at least of a sulfated polysaccharide, APS and resveratrol and/or sialic acid and combinations thereof. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and diglycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

Servings of the nutritional supplement preferably contain for example, a daily dosage of between 2 g and 10.0 g of the sulfated polysaccharide (e.g., fucoidan) or between 10 and 20 g of the sulfated polysaccharide, preferably between 3.0 g and 5.0 g of the sulfated polysaccharide (e.g., fucoidan); a daily dosage of resveratrol of from 1 to 100 mg, from 1 to 50 mg, or from 1 to 20 mg daily; APS in a daily dosage of from 0.1-10 grams of the APS, and most preferably from 0.5-5 grams of the APS or 0.5 to 3 grams of the APS; and/or a daily dosage of a sialic acid of from between 0.1 g and 10.0 g of sialic acid, preferably between 0.5 g and 2.0 g of sialic acid, and even more preferably, approximately 1.0 g of sialic acid. It is understood by those of skill in the art that other ingredients can be added to those described herein, for example, fillers, emulsifiers, preservatives, etc. for the processing or manufacture of a nutritional supplement.

I. Food Products

In still further embodiments, the present invention provides functional foods, including food products, prepared food products, or foodstuffs comprising at least one of a sulfated polysaccharide (e.g., fucoidan), APS and resveratrol. For example, in some embodiments, beverages and solid or semi-solid foods comprising sulfated polysaccharides (e.g., fucoidan) are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

Servings of the food product preferably contain between 1.0 g and 10.0 g of the sulfated polysaccharide (e.g., fucoidan), preferably between 3.0 and 5.0 g of the sulfated polysaccharide (e.g., fucoidan).

EXAMPLES

Example 1

3-5 grams of a macroalgae extract containing approximately 70-80% sulfated polysaccharides was administered to human subjects for a twelve week period. At the end of the eight week period, the subjects reported an average decrease in body fat of from 5-10% with no change in diet or training. The subjects also reported no colds or flu during the eight-week period. The results are shown in the following table.

Example 2

Effect of *Astragalus* Polysaccharide (APS) on AD-36

Solubility Test:

*Astragalus* Polysaccharide extract were dissolved in phosphate-buffered saline (PBS) at 10 mg/ml. The solution was cleared by centrifugation and the supernatant fraction was filtered through a 24 um filter to sterilize.

Figure 2:
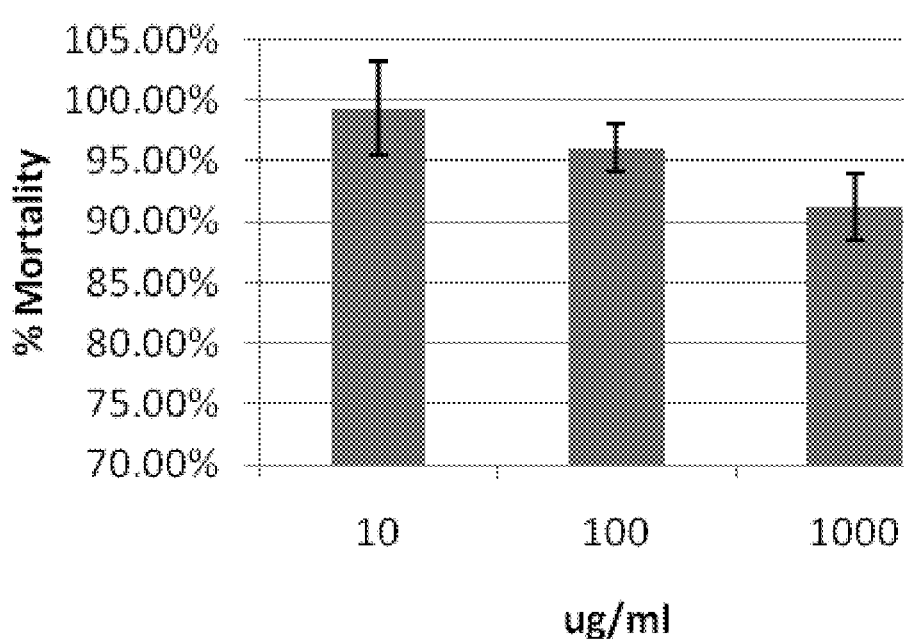
FIG. 2. APS cytotoxicity in 3T3-L1.

Cytotoxicity of APS in A549 Cells and 3T3-L1:

nine serial 1:10 dilutions with the highest concentration at 1 mg/ml were tested. Each concentration has 8 replicates. In 3T3-L1 cells, 1 mg/ml and two 10 fold dilutions were tested. Each concentration has 6 replicates. O.D. value indicates viability of the cells. O.D. value indicates viability of the cells. APS does not show any toxicity to A549 (FIG. 1). APS does not have a detrimental effect on 3T3-L1 (7% death rate at 1 mg/ml) (FIGS. 1 and 2).

Figure 3:
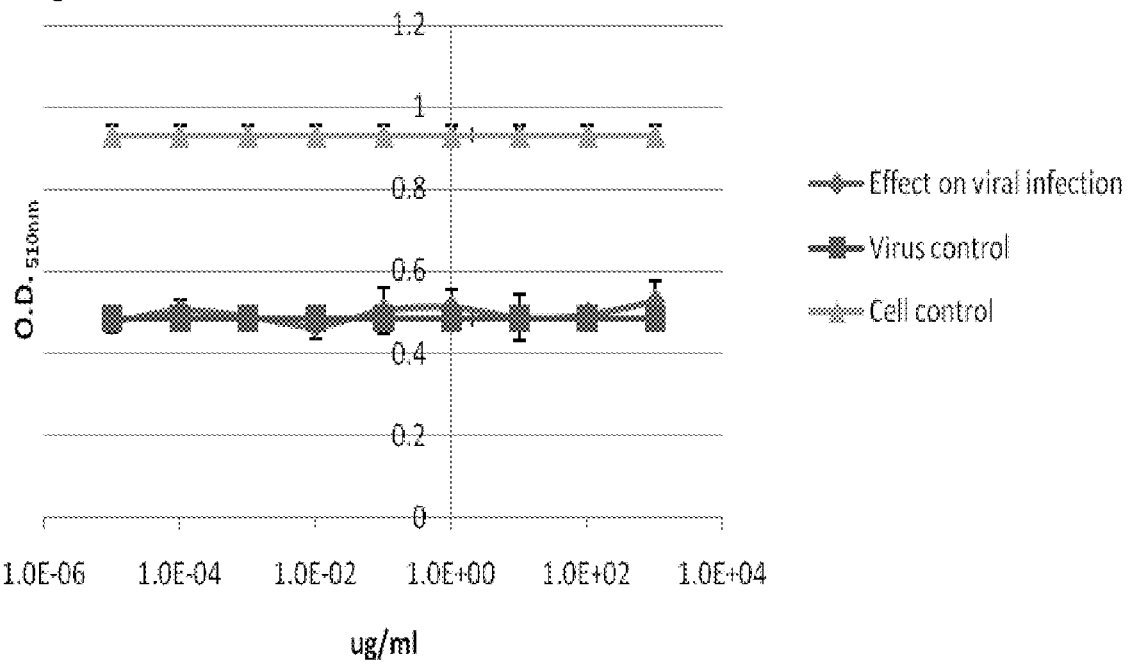
FIG. 3. Effect of APS on viral infection (MTT method).
Figure 4:
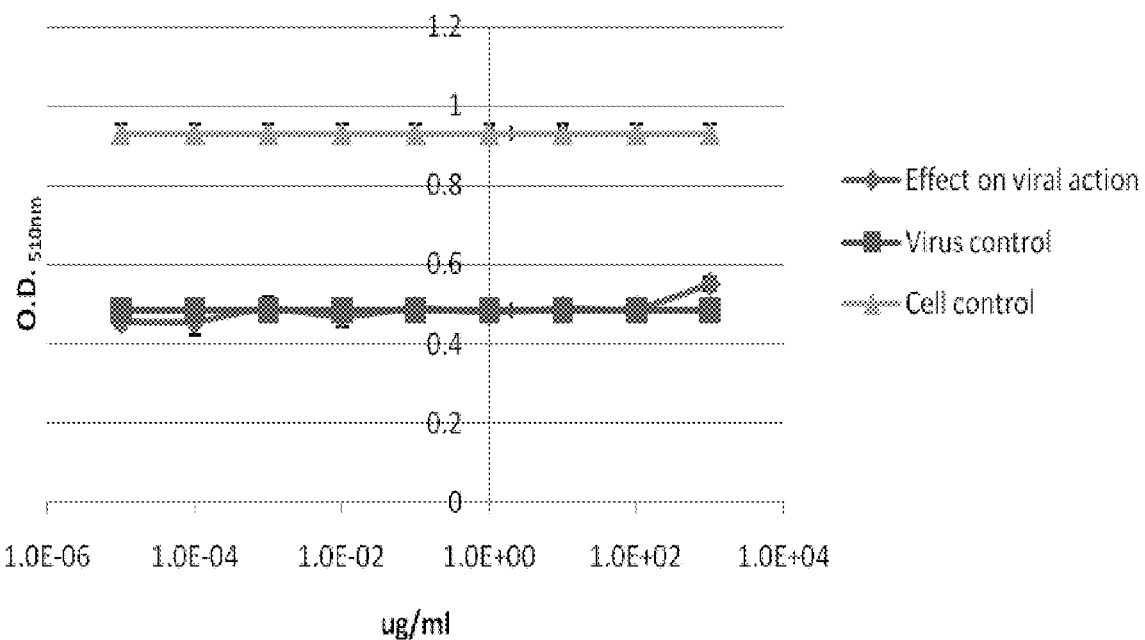
FIG. 4. Effect of APS on viral action (MTT method).

Effect of APS on Viral Infection and Action:

Cells were treated as indicated in the contract. The cells were incubated with fixed amount of virus (100 TCID/well), but with serial dilutions of APS. The viability of the cells was determined by MTT reagent and a dose-responsive curve was generated. The lower O.D. value indicates the more cell death induced by Ad36. Cell control (cells only, no virus, no drug) and virus control (cells and virus, no drug) were included in each experiment. APS does not have strong antiviral activity against Ad36 (FIG. 3 and FIG. 4). Raw data is listed in Table 2.

|  | Male 1 Age 28 | Male 2 Age 35 | Male 3 Age 41 | Male 4 Age 22 | Male 5 Age 17 | Male 6 Age 49 | Male 7 Age 48 |
|---|---|---|---|---|---|---|---|
| WEEK 1 | | | | | | | |
| Body fat (%) | 36 | 28 | 50 | 25 | 31 | 24 | 33 |
| BW (kg) | 110 | 82 | 98 | 76 | 83 | 101 | 105 |
| BP | 95 | 105 | 70 | 80 | 65 | 135 | 125 |
| Health | healthy | healthy | Obese | Slight flu | Sinus | Slight cold | healthy |
| WEEK 12 | | | | | | | |
| Body fat (%) | 29 | 21 | 39 | 18 | 21 | 18 | 26 |
| BW (kg) | 105 | 81 | 89 | 78 | 78 | 90 | 103 |
| BP | 107.5 | 112.5 | 95 | 92.5 | 85 | 145.5 | 132.5 |
| Health | No cold/flu | Slight hayfever | No cold/flu | No cold/flu | No sinus/cold/flu | No cold/flu | No cold/flu |

TABLE 2

Raw data of APS antiviral testing (MTT method)

| Condition | Sample cell viability (O.D.$_{510\,nm}$) | virus control cell viability (O.D.$_{510\,nm}$) | cell control cell viability (O.D.$_{510\,nm}$) | Inhibition of virus activity (%) |
|---|---|---|---|---|
| Effect on viral infection | | | | |
| 1000 ug/ml | 0.526 ± 0.052 | 0.484 ± 0.019 | 0.931 ± 0.023 | 8.60 ± 10.82 |
| 100 ug/ml | 0.494 ± 0.015 | 0.484 ± 0.019 | 0.931 ± 0.023 | 2.00 ± 3.20 |
| 10 ug/ml | 0.487 ± 0.057 | 0.484 ± 0.019 | 0.931 ± 0.023 | 0.59 ± 11.95 |
| 1 ug/ml | 0.511 ± 0.044 | 0.484 ± 0.019 | 0.931 ± 0.023 | 5.70 ± 9.14 |
| 1.0E−01 ug/ml | 0.503 ± 0.056 | 0.484 ± 0.019 | 0.931 ± 0.023 | 4.01 ± 11.68 |
| 1.0E−02 ug/ml | 0.466 ± 0.031 | 0.484 ± 0.019 | 0.931 ± 0.023 | −3.66 ± 6.56 |
| 1.0E−03 ug/ml | 0.489 ± 0.024 | 0.484 ± 0.019 | 0.931 ± 0.023 | 1.00 ± 5.03 |
| 1.0E−04 ug/ml | 0.503 ± 0.026 | 0.484 ± 0.019 | 0.931 ± 0.023 | 3.98 ± 5.57 |
| 1.0E−05 ug/ml | 0.476 ± 0.023 | 0.484 ± 0.019 | 0.931 ± 0.023 | −1.69 ± 4.87 |
| Effect on viral action | | | | |
| 1000 ug/ml | 0.550 ± 0.016 | 0.467 ± 0.015 | 0.765 ± 0.023 | 13.7 ± 3.46 |
| 100 ug/ml | 0.490 ± 0.019 | 0.467 ± 0.015 | 0.765 ± 0.023 | 1.25 ± 4.03 |
| 10 ug/ml | 0.489 ± 0.016 | 0.467 ± 0.015 | 0.765 ± 0.023 | 1.03 ± 3.37 |
| 1 ug/ml | 0.479 ± 0.016 | 0.467 ± 0.015 | 0.765 ± 0.023 | −1.05 ± 3.34 |
| 1.0E−01 ug/ml | 0.490 ± 0.010 | 0.467 ± 0.015 | 0.765 ± 0.023 | 1.17 ± 2.07 |
| 1.0E−02 ug/ml | 0.469 ± 0.026 | 0.467 ± 0.015 | 0.765 ± 0.023 | −3.09 ± 5.48 |
| 1.0E−03 ug/ml | 0.488 ± 0.027 | 0.467 ± 0.015 | 0.765 ± 0.023 | 0.91 ± 5.73 |
| 1.0E−04 ug/ml | 0.456 ± 0.032 | 0.467 ± 0.015 | 0.765 ± 0.023 | −5.76 ± 6.73 |
| 1.0E−05 ug/ml | 0.455 ± 0.017 | 0.467 ± 0.015 | 0.914 ± 0.057 | −5.85 ± 3.59 |

Antiviral Testing for APS Possessing Weaker Antiviral Activity:

In this assay, titer of control virus and the virus with compound treatment were determined. Titer is determined by measuring TCID$_{50}$ which is the direct reflection of virulence of virus. The higher the TCID$_{50}$ is, the more virulent the virus is. A given compound showing any antiviral activity will result in lower TCID$_{50}$ value compared to control virus.

Initial screening: In the Initial screening, only one concentration of APS is tested, which is the highest concentration that is not toxic to A549 cells. This initial screening does not differentiate where the antiviral activity occurs, preventing infection or inhibiting virus action/replication, or killing virus directly. Cells and virus were both pretreated with the APS for 5 hrs, and incubated in the APS chronically during the experiment. TCID$_{50}$/ml was calculated by the Reed-Muench formula. Conclusion: 1 mg/ml APS reduces Ad36 activity by 96.84% (FIG. 5).

Assessment of APS antiviral effect on viral infection, viral action/replication, or virus itself (two concentrations of APS tested, 1 mg/ml and 10 ug/ml). The cells were treated with fixed concentration of APS (1 mg/ml or 10 ug/ml), but with serial dilutions of Ad36. Each condition has 8 replicates. Each plate has cell and virus control. After 3 days in culture, cell death was examined by microscope and % cytotoxicity was calculated. Titer of control virus and the virus with compound treatments were also determined. The five different treatments are listed as following:

| | 3 days incubation in: |
|---|---|
| 1. Control plate (no treatment): cells + virus | → medium |
| 2. APS pretreated cells + pretreat virus | → APS |
| 3. APS pretreated cells + virus | → medium |
| 4. Cells + virus | → APS |
| 5. APS pretreated cells + virus | → APS |

Figure 6:
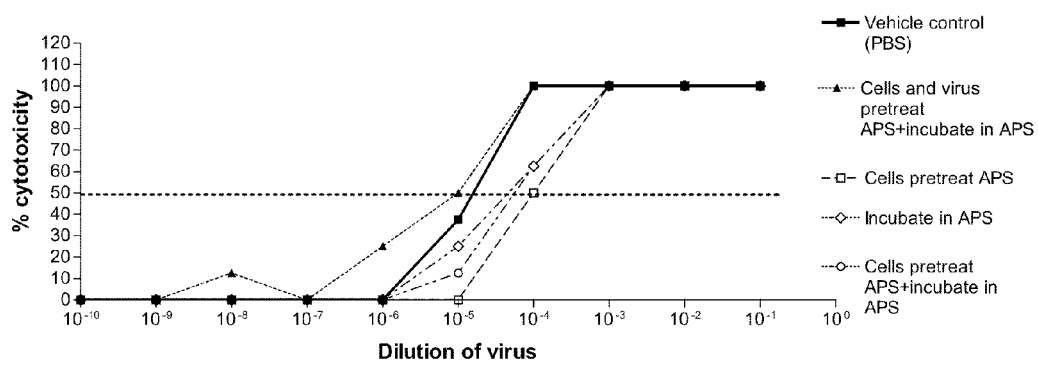
FIG. 6. Antiviral activity of APS (10 ug/ml) by TCID method.

Referring to FIG. 6, Y axis represents the % of cell death. X axis is the viral dilutions. APS tested is 10 ug/ml. The dotted line indicates where 50% cell death occurs. Any treatment reduces viral activity will shift the vehicle control plot to the right. Viral activity significantly reduces when cells were pretreated or incubated in APS (B, C and D). Conclusion: APS (10 ug/ml) protect cells from infection and reduces viral action.

Figure 7:
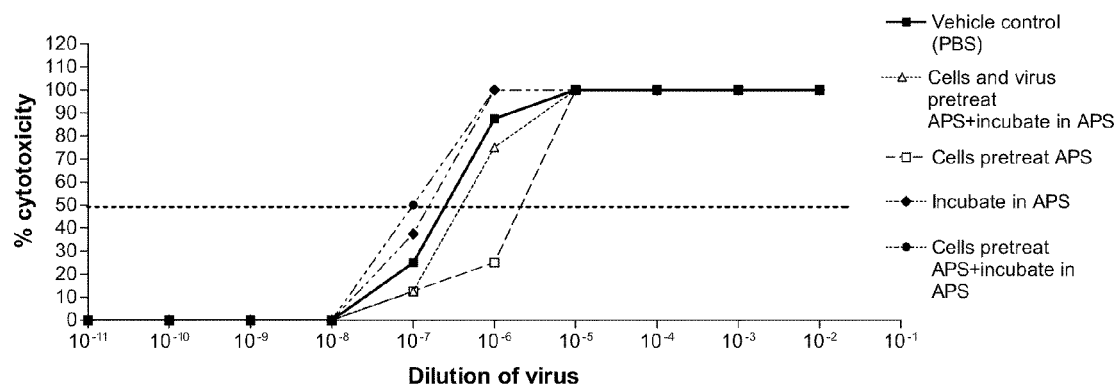
FIG. 7. Antiviral activity of APS (1 mg/ml) by TCID method.
Figure 8:
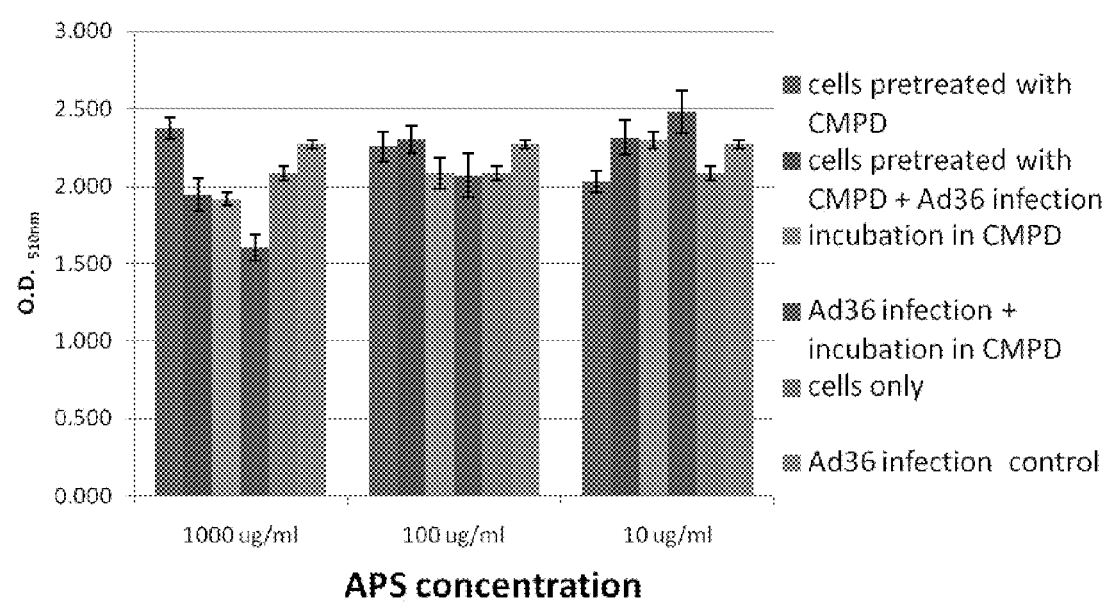
FIG. 8. Effect of APS on 3T3-L1 differentiation (Oil-red O staining).

Referring to FIG. 7, APS shows profound antiviral activity when cells are pretreated (B). However, cell death increases when cells are incubated in APS (C, D). This increased cell death can be due to APS enhancing viral activity or it simply kills the infected cells. Since low concentration of APS does not promote viral activity, it is more likely the high concentration of APS is toxic to infected cells. APS kills virus directly. Virus activity reduces when virus pretreated with APS (A) compared to non-pretreated condition (D). Conclusion: APS (1 mg/ml) inhibits viral infection and has virucidal effect.

Effect of APS on Viral Infection and Viral Action in 3T3-L1 Adipocytes.

Mock-infected 3T3-L1 or Ad36-infected 3T3-L1 were pretreated or incubated with APS at 3 different concentrations: 1 mg/ml, 100 ug/ml or 10 ug/ml. The fat accumulation was stained by Oil-red O at day 5 post infection. Conclusion: In adipocytes, concentration higher than 100 ug/ml (especially at 1 mg/ml) prevents infection and inhibits Ad36 induced fat accumulation.

Example 3

Effect of Fucoidan on AD-36

Solubility Test:

The stock solution was prepared according to the literature. Fucoidan (80% purity) was dissolved in phosphate-buffered saline (PBS) at 10 mg/ml. The solution was cleared by centrifugation and the supernatant fraction was filtered through a 24 um filter to sterilize. There was a large amount of precipitate in the Fucoidan preparation and the solution was very hard to filter.

Figure 9:
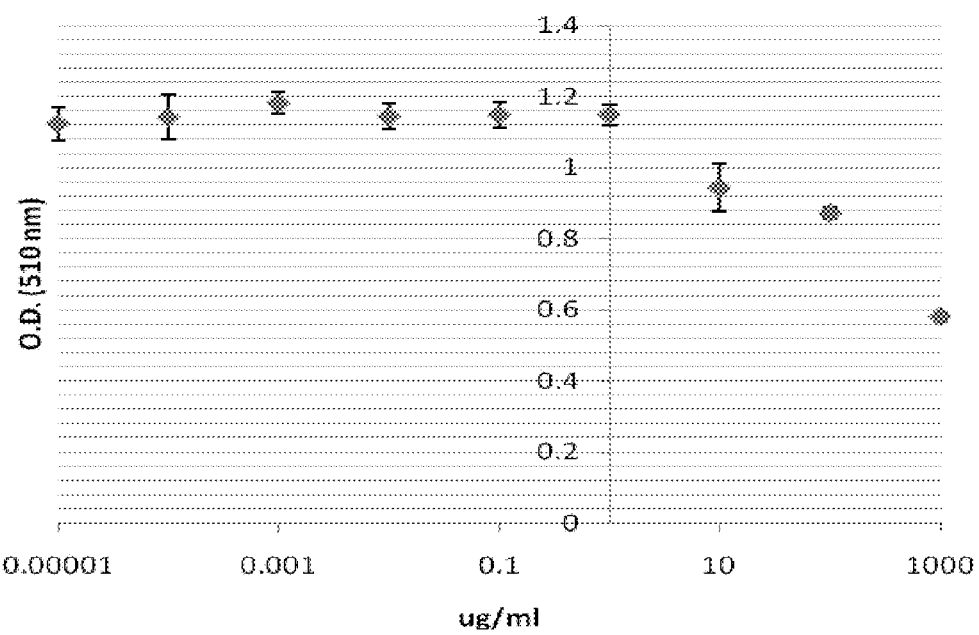
FIG. 9. Fucoidan (purity 80%) cytotoxicity in A549 cells.
Figure 10:
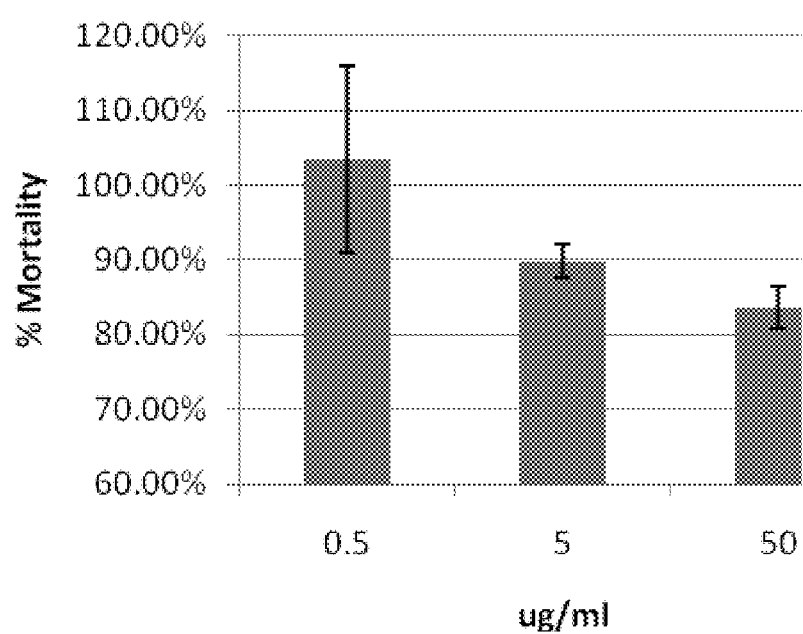
FIG. 10. Fucoidan (80% purity) cytotoxicity in 3T3-L1 cells.

Cytotoxicity of Fucoidan in A549 Cells and 3T3-L1:

In A549 cells, nine serial 1:10 dilutions with the highest concentration at 1 mg/ml were tested. Each concentration has 8 replicates. In 3T3-L1 cells, 50 ug/ml and two 10 fold dilutions were tested. Each concentration has 6 replicates. O.D. value indicates viability of the cells. Fucoidan kills cells when concentration is higher than 1 ug/ml. Fucoidan shows minimal toxicity to 3T3-L1 cells at concentration higher than 5 ug/ml (20% death at 50 ug/ml). See FIGS. 9 and 10.

Figure 11:
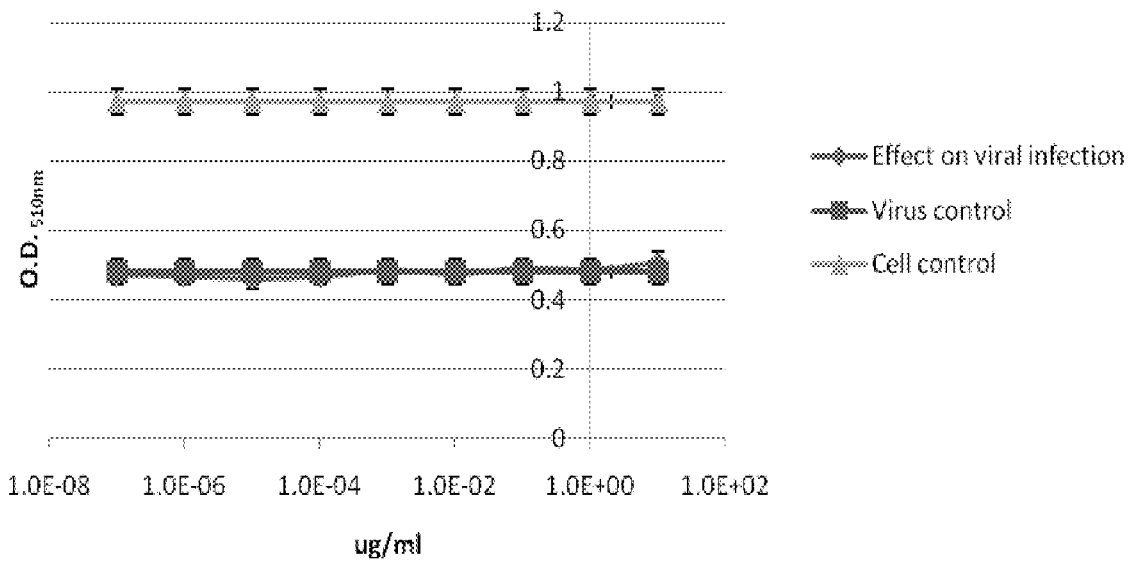
FIG. 11. Effect of Fucoidan on viral infection (MTT method).
Figure 12:
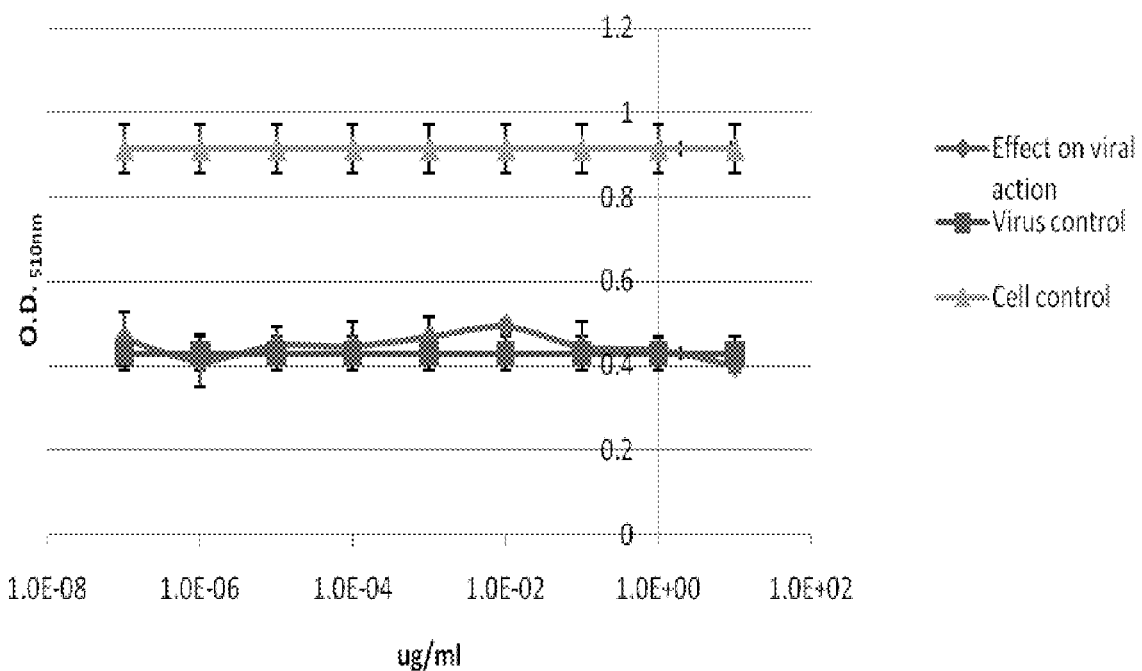
FIG. 12. Effect of Fucoidan on viral action (MTT method).

Effect of Fucoidan on Viral Infection and Action:

Cells were treated as indicated in the contract. The cells were incubated with fixed amount of virus (100 TCID/well), but with serial dilutions of Fucoidan. The viability of the cells was determined by MTT reagent and a dose-responsive curve was generated. The lower O.D. value indicates the more cell death induced by Ad36. Cell control (cells only, no virus, no drug) and virus control (cells and virus, no drug) were included in each experiment. Fucoidan does not have strong antiviral activity against Ad36 (FIGS. 11 and 12). Raw data is listed in Table 3.

TABLE 3

Raw data of Fucoidan antiviral testing (MTT method)

| Condition | Sample cell viability (O.D.$_{510\,nm}$) | virus control cell viability (O.D.$_{510\,nm}$) | cell control cell viability (O.D.$_{510\,nm}$) | Inhibition of virus activity (%) |
|---|---|---|---|---|
| Effect on viral infection | | | | |
| 10 ug/ml | 0.507 ± 0.031 | 0.480 ± 0.036 | 0.971 ± 0.036 | 5.51 ± 6.64 |
| 1 ug/ml | 0.486 ± 0.008 | 0.480 ± 0.036 | 0.971 ± 0.036 | 1.17 ± 1.86 |
| 1.0E−01 ug/ml | 0.490 ± 0.007 | 0.480 ± 0.036 | 0.971 ± 0.036 | 1.95 ± 1.31 |
| 1.0E−02 ug/ml | 0.474 ± 0.029 | 0.480 ± 0.036 | 0.971 ± 0.036 | −1.27 ± 6.15 |
| 1.0E−03 ug/ml | 0.484 ± 0.008 | 0.480 ± 0.036 | 0.971 ± 0.036 | 0.88 ± 1.81 |
| 1.0E−04 ug/ml | 0.465 ± 0.022 | 0.480 ± 0.036 | 0.971 ± 0.036 | −3.13 ± 4.68 |
| 1.0E−05 ug/ml | 0.459 ± 0.029 | 0.480 ± 0.036 | 0.971 ± 0.036 | −4.44 ± 6.21 |
| 1.0E−06 ug/ml | 0.467 ± 0.021 | 0.480 ± 0.036 | 0.971 ± 0.036 | −2.78 ± 4.42 |
| 1.0E−07 ug/ml | 0.470 ± 0.013 | 0.480 ± 0.036 | 0.971 ± 0.036 | −2.13 ± 2.90 |
| Effect on viral action | | | | |
| 10 ug/ml | 0.400 ± 0.016 | 0.428 ± 0.041 | 0.914 ± 0.057 | −6.60 ± 3.82 |
| 1.0E+00 ug/ml | 0.437 ± 0.029 | 0.428 ± 0.041 | 0.914 ± 0.057 | 1.95 ± 6.93 |
| 1.0E−01 ug/ml | 0.445 ± 0.058 | 0.428 ± 0.041 | 0.914 ± 0.057 | 3.80 ± 13.51 |
| 1.0E−02 ug/ml | 0.493 ± 0.014 | 0.428 ± 0.041 | 0.914 ± 0.057 | 15.19 ± 3.46 |
| 1.0E−03 ug/ml | 0.468 ± 0.046 | 0.428 ± 0.041 | 0.914 ± 0.057 | 9.30 ± 10.94 |
| 1.0E−04 ug/ml | 0.447 ± 0.056 | 0.428 ± 0.041 | 0.914 ± 0.057 | 4.30 ± 13.22 |
| 1.0E−05 ug/ml | 0.448 ± 0.044 | 0.428 ± 0.041 | 0.914 ± 0.057 | 4.71 ± 10.44 |
| 1.0E−06 ug/ml | 0.412 ± 0.061 | 0.428 ± 0.041 | 0.914 ± 0.057 | −3.80 ± 14.26 |
| 1.0E−07 ug/ml | 0.464 ± 0.064 | 0.428 ± 0.041 | 0.914 ± 0.057 | 8.40 ± 14.96 |

Antiviral Testing for Fucoidan Possessing Weaker Antiviral Activity:

In this assay, titer of control virus and the virus with compound treatment were determined. Titer is determined by measuring TCID$_{50}$ which is the direct reflection of virulence of virus. The higher the TCID$_{50}$ is, the more virulent the virus is. A given compound showing any antiviral activity will result in lower TCID$_{50}$ value compared to control virus.

Figure 13:
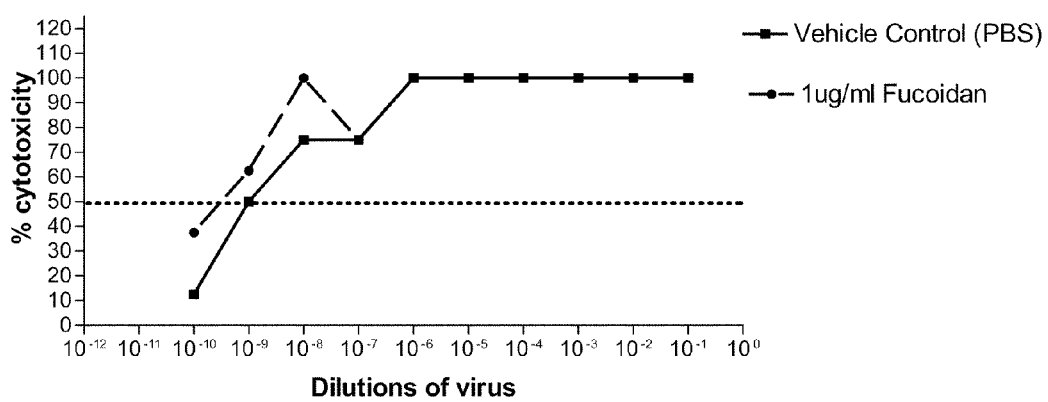
FIG. 13. Initial screening of Fucoidan for weaker antiviral activity.

Initial screening: In the Initial screening, only one concentration of an agent is tested, which is the highest concentration that is not toxic to A549 cells. This initial screening does not differentiate where the antiviral activity occurs, preventing infection or inhibiting virus action/replication, or killing virus directly. Cells and virus were both pretreated with the Fucoidan for 5 hrs, and incubated in the Fucoidan chronically during the experiment. TCID$_{50}$/ml was calculated by the Reed-Muench formula. Conclusion: Fucoidan does not have any antiviral activity (FIG. 13).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

I claim:

1. A method of inhibiting infection by Ad-36 and related fat accumulation in a subject comprising:
    orally administering a composition comprising fucoidan and an effective amount of *Astragalus* polysaccharide to said subject under conditions that infection by Ad-36 and related fat accumulation are inhibited, wherein said effective amount of *Astragalus* polysaccharide is from about 0.1 to 10 grams.

2. The method of claim 1, further comprising administering an agent selected from the group consisting of a flavonoid and a sialic acid.

3. The method of claim 1, wherein said composition further comprises resveratrol.

4. The method of claim 1, wherein said administration of said composition induces weight reduction in a subject.

5. The method of claim 1, wherein said administration of said composition increases the lean body mass of said subject.

6. The method of claim 1, wherein said administration of said composition reduces cellulite in said subject.

7. The method of claim 1, wherein said administration of said composition reduces body fat in said subject.

8. The method of claim 1, wherein said composition is a dietary supplement.

9. The method of claim 1, wherein said composition is a nutritional supplement.

10. The method of claim 1, wherein said composition is provided in a food or a drink.

11. The method of claim 1, wherein said fucoidan is from a natural source selected from the group consisting of marine brown algae and sea cucumbers.

12. The method of claim 11, wherein said fucoidan is administered in a daily dosage of from 3 to 5 grams.

13. The method of claim 4, wherein said resveratrol is administered in a daily dosage of from about 1 mg to 50 mg.

14. The method of claim 4, wherein said *Astragalus* polysaccharide is administered in a daily dosage of from 0.5 to 5 grams.

\* \* \* \* \*